United States Patent [19]

Hedrick

[11] 4,071,030

[45] Jan. 31, 1978

[54] ROTATABLE DURAGUARD

[75] Inventor: John R. Hedrick, La Crescenta, Calif.

[73] Assignee: Pevrick Engineering Company, Inc., Sun Valley, Calif.

[21] Appl. No.: 675,709

[22] Filed: Apr. 12, 1976

[51] Int. Cl.² .................... A61B 17/16; B26B 29/00
[52] U.S. Cl. ................................ 128/310; 30/276; 30/286
[58] Field of Search ............ 128/305, 305.1, 310, 128/317; 30/276, 286

[56] References Cited

U.S. PATENT DOCUMENTS

| 983,368 | 2/1911 | Holt | 128/310 UX |
|---|---|---|---|
| 1,771,764 | 7/1930 | Beattie | 30/276 |
| 3,384,085 | 5/1968 | Hall | 128/305.1 |
| 3,750,671 | 8/1973 | Hedrick | 128/305 |

*Primary Examiner*—Channing L. Pace
*Attorney, Agent, or Firm*—Robert E. Geauque

[57] ABSTRACT

A duraguard for a surgical cutting tool consisting of a guard mounting member rotatably mounted within the nose section of the tool housing at two spaced locations and supporting a guard arm extending outwardly along the cutting tool and terminating a protective foot extending over the end of the cutting tool to separate the dura from the skull, the arm and foot being rotatable relative to and about the cutting tool in order to follow curved slots formed by the tool.

5 Claims, 3 Drawing Figures

ROTATABLE DURAGUARD

BACKGROUND OF THE INVENTION

A guard known as a "duraguard" is utilized with a small rotating cutting tool in brain surgery to move the dura layer away from the inner skull surface as the cutting tool is moved to cut an opening in the skull. The guard consists of an arm fixed at one end to the cutting tool housing and having a foot at the outer end which covers and is spaced slightly from the end of the cutting tool. The foot enters between the skull and the dura and serves to move the dura away from the inner skull surface should it be stuck to the skull surface, thereby preventing the tool from cutting anything but the skull itself. During the skull cutting operation, the arm follows in the cut made by the tool and the foot projects slightly ahead of the outer tip of the cutting tool. With the arm and foot fixed to the end of the housing and fixed relative to the axis of the cutting tool extending from the end of the housing, it is difficult to cut curved lines or corners with the instrument since the arm of the guard wants to follow directly to the location of the cutting tool. Thus, when the cutting tool executes a sharp curve, the arm wants to cut across the curved portion between the arm and the cutting tool. Therefore, it is necessary to rotate the tool housing while moving the cutting tool in order for the arm to follow in the curved slot already cut in the skull by the cutting tool. When the fixed duraguard is used to cut a complete round opening, it requires the switching of hands on the tool in order to move the tool in different directions and keep the duraguard following as well as possible.

Since the arm is required to follow through the slit in the skull, the foot and arm can be forced against the blade and thereby damage to both the blade and the guard can occur. After the duraguard arm is bent, it is hard to align since the end of the duraguard must be opposite the cutting tool at all times and it is usually necessary to return the complete cutting tool to the factory for replacement of the guard. There have been attempts made to produce swiveling duraguards which rotate on the end of the cutting tool housing but no device has been produced which removes the tendency of the foot to move against the blade and when this happens, the duraguard will get cut up by the blade or generates heat which is undesirable during the cutting operation.

SUMMARY OF THE INVENTION

The present invention provides a duraguard consisting of an arm and a foot located slightly from the end of the cutting tool as in the earlier device. However, the end of the arm is rotatably mounted in the end of the tool housing for rotation about the axis of the cutting tool while holding the foot at the outer end spaced slightly from the end of the cutting tool. A guard mounting member is rotatably supported in the nose section of the cutting tool housing and the end of the arm is attached to this member so that as the cutting tool makes a slot in the skull, the arm can rotate about the tool in order to follow the slot without having to move the tool housing. At sharp turns, the arm will be free to follow the slot in the skull even though the direction of movement of the cutting tool has changed sharply. The guard mounting member is rotatably supported at two spaced locations in its nose section of the housing in order to keep the duraguard accurately located with respect to the cutting tool. Two separate sets of ball bearings are contained in offset portions of the nose section and these ball bearings cooperate with the guard mounting member to accurately align the duraguard arm with respect to the cutting tool.

A locking device in the end of the nose section forces both sets of ball bearings outwardly against the internal surface of the nose section so that it is possible to slightly preload the bearings and thereby eliminate the necessity of holding close tolerances on the bearings. The mounting structure for the duraguard of the present invention prevents the guard from moving over into contact with the blade because alignment of the guard arm is accurately maintained while the arm is following a curve in the tool cut. The invention prevents the guard from being cut up or from generating heat because of contact with the rotating cutting tool.

BRIEF DESCRIPTION OF THE SHOWN EMBODIMENT

Figure 1:
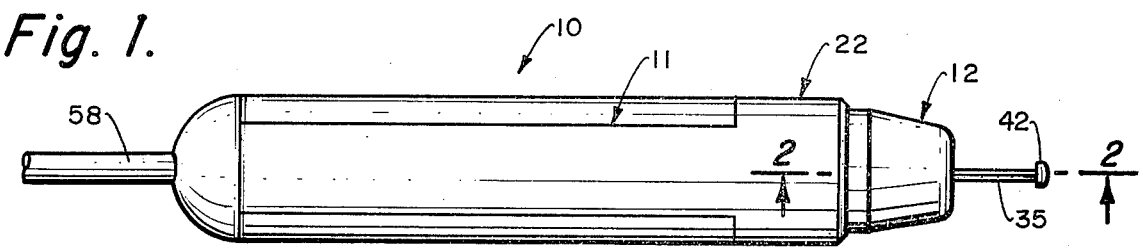
FIG. 1 is an elevational view of a cutting tool with a rotating or swiveling duraguard.
Figure 2:
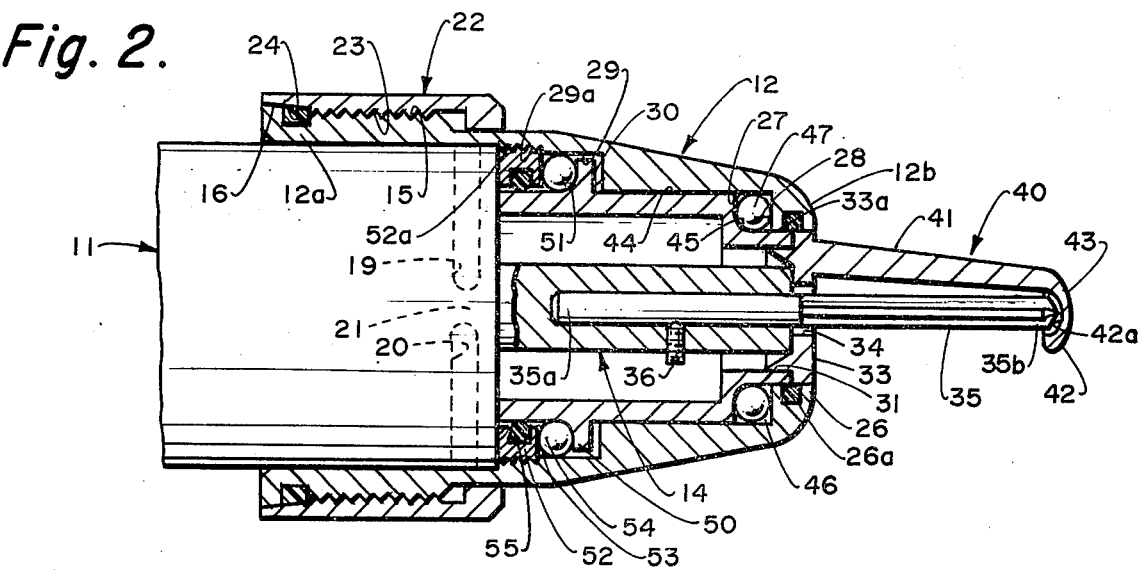
FIG. 2 is a horizontal section along line 2—2 of FIG. 1 showing the nose section attached to the tool housing and rotatably mounting the duraguard arm and foot.
Figure 3:
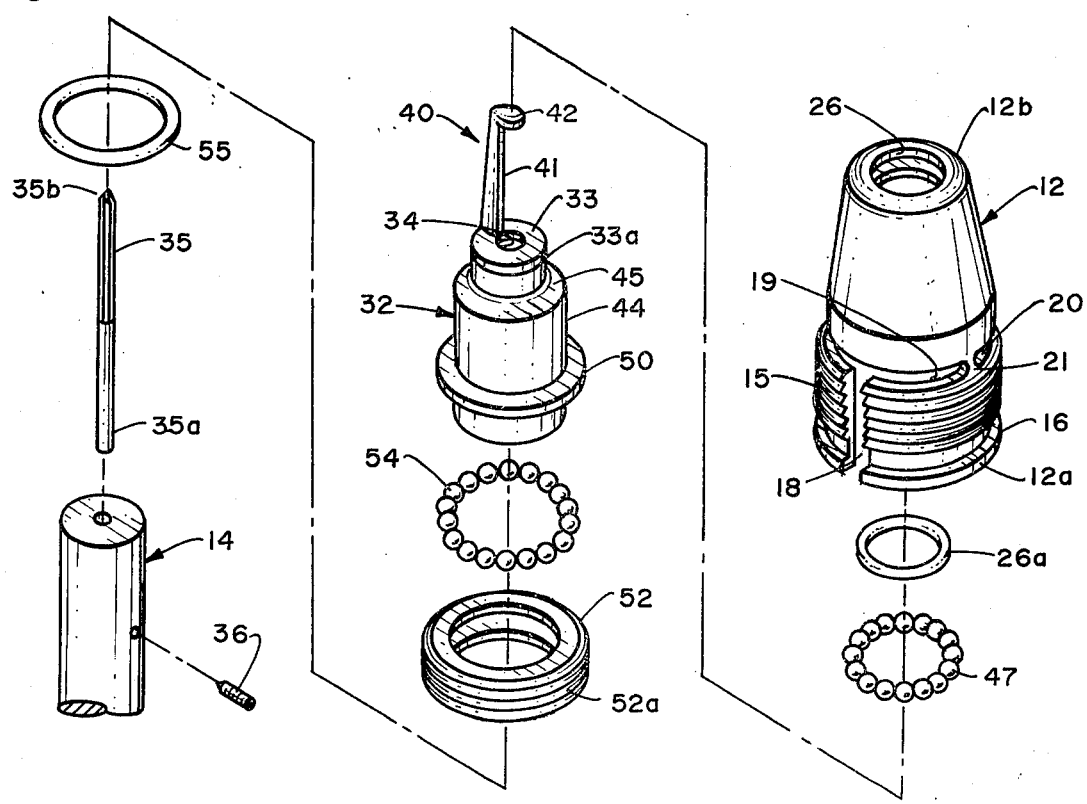
FIG. 3 is a perspective view of the nose section and guard mounting member.

The cutting tool 10 has a housing 11 and hollow housing nose section 12 is placed over the end of the housing. The cutting tool comprises a rotating air turbine (not shown) which rotatably drives shaft 14 extending from the end of the housing 11. The end of housing 11 is inserted into end 12a of nose section 12 which has external threads 15 and an outwardly tapered surface 16. Also, nose section end 12a contains longitudinal slots 18 (See FIG. 3) and transverse slots 19 and 20 separated from one another by sections 21. A cylindrical retaining ring 22 has internal threads 23 which receive threads 15 and has an internal tapered surface 24 which engages surface 16 on the nose section. When the ring 22 is threaded onto the nose section 12, tapered surface 24 engages surface 16 and forces the end 12a of the nose section against the end of the housing 11 because of the flexibility in end 12a provided by the slots 18, 19 and 20. This attachment structure is standard for nose sections which carry a rigid duraguard.

The interior surface of nose section 12 has a first cylindrical surface section 26 defining an end opening, a second cylindrical surface section 27 connected to the first surface section by a first flange section 28, and a third cylindrical surface section 29 connected to the second surface section by a second flange section 30. The end surface section 26 contains O-ring 26a. Guard mounting member 32 has an end 33 with a surface 33a rotatably mounted in nose section surface 26. End 33 has an opening 34 through which projects a cutting tool 35 and cylindrical end 35a of the tool is secured in a socket opening in the end of shaft 14 by means of a lock screw 36 or other suitable holding device so that the tool 35 rotates with shaft 14. Guard 40 comprises an arm 41 which is secured to end 31 of the mounting member 32 and extends outwardly along tool 35 and terminates in foot 42 which has a cup-shaped surface 42a spaced slightly from the end of the tool. Outer surface 43 is smoothly curved and projects past the tool end so that it proceeds the cutting tool and separates the dura from the skull ahead of the cutting tool, thereby, preventing damage to the dura.

Surface 33a of the mounting member is connected with an enlarged cylindrical surface portion 44 by means of a first curved surface 45 which is located opposite flange 28 of the nose section to form a curved space 46 for a set of ball bearings 47. A part of surface 44 is rotatably engaged with surface 27 of the nose section and beyond surface 27, a circular projection 50 extends outwardly from surface 44 and has a curved surface 51 on one side thereof. A retainer nut 52 forms a flange located around the end of surface portion 44 and has threads 52a threaded to threads 29a on the interior of surface 29 of nose section 12. The side of nut 52 and the curved surface 51 form a curved space 53 for a set of ball bearings 54, and nut 52 has a cut-out for O-ring 55 which bears against the end of surface 44 of mounting member 32. The curved surfaces 45 and 51 have a slightly larger radius of curvature than the radius of the balls 47 and 54, respectively, so that when nut 52 is threaded inwardly, it engages the balls and forces the balls outwardly against the surfaces 27 and 29, respectively, of the nose section 12 so that the bearing can be preloaded to maintain the mounting member 32 concentric with the nose section 12 without keeping close tolerances. It is advisable to utilize a locking agent to secure the threads 52a to the threads 29a so that once the preload has been set the retaining nut 52 cannot become accidentally loosened. Since the preload upon the bearings maintain the mounting member 32 concentric with the axis of rotation of the shaft 14, the arm 41 and the foot 42 will not be pushed into engagement with the end 35b of the cutting tool thereby damaging the foot 42 and possibly damaging the cutting tool during the cutting operation. The arm will follow the cut made by the tool 35 and when it is necessary to change direction this can be done without changing hands since the arm will follow the cut in the skull and will not bind while changing direction. Because of the rotatable mounting of the mounting member supporting the arm, the arm will not be bent into the tool during change in tool direction thus preventing the tool cutting the arm and generating heat.

To assemble the device, the ball bearings 47 are placed on surface 45 and then the arm 41 is inserted through the opening 26 in the nose section so that the balls engage the flange section 28. Thereafter, balls 54 are inserted against the curved surface 51 and the retaining nut 52 is tightened onto the threads 29a until the desired preload on boths sets of ball bearings is obtained. The nose section 12 is then placed over the housing 11 until the end of the housing is adjacent the retaining nut 52 and then the threaded retaining ring 22 is tightened down in order to flex the end 12a of the nose section into contact with the end of housing 11. The air for the turbine which drives the shaft 14 is introduced through passage 58 and the tool 35 is rotated at the correct speed. The housing 11 is gripped by the hand to hold the tool at the desired angle to the skull so that the tool cuts the desired slot in the skull.

What is claimed is:

1. A duraguard mounted by a hollow nose section secured to the housing of a cutting tool, the duraguard having an arm extending along the cutting tool and terminating in a foot projecting over the end of the cutting tool, the improvement comprising:

means for securing said nose section to one end of said housing from which said cutting tool extends, said nose section having an interior surface defining a hollow interior space;

a guard mounting member located in said nose section;

means for rotatably mounting said guard mounting member on said nose section for free rotation about the axis of said tool;

one end of said arm being secured to said guard mounting member;

said foot being secured to the other end of said arm and projecting over the end of said cutting tool, and said arm being free to rotate and follow the cut produced by said cutting tool;

said mounting means comprising two separate sets of ball bearings located between said guard mounting member and said nose section and positioned adjacent opposite ends of said guard mounting member; and each set of ball bearings consisting of a circular row of ball bearings around said guard mounting member, each row of ball bearings being located in a space between a radially projecting planar flange surface and a radially projecting contoured surface, one of said surfaces for locating each of said rows being located on said interior surface of said nose section and the other of said surfaces being located on the exterior of said guard mounting member.

2. A duraguard as defined in claim 1:

said planar flange surface for each of said rows being located on said interior surface of said nose section and said contoured surface for each of said rows being located on said guard mounting member.

3. A duraguard as defined in claim 1:

said spaces for said rows being closed by different portions of said interior surface of said nose section;

each of said contoured surfaces having a radius of curvature larger than the radius of said ball bearings contained in said space; and one of said flange surfaces comprising an annular nut threaded onto said interior surface of said nose section and engaging the ball bearings of one set, the tightening of said nut forcing each said sets of ball bearings against its contoured surface and against one of said portions of said interior surface of said nose section in order to preload both sets of bearings and position said guard mounting member concentric with said nose section.

4. A duraguard as defined in claim 3:

said interior surface of said nose section having a first cylindrical surface section at one end adjacent said arm and a second cylindrical section located adjacent said one end of said housing;

said guard mounting member having separate first and second cylindrical surface portions rotatably supported on said surface sections; and said arm projecting from said first cylindrical surface section.

5. A duraguard as defined in claim 4:

one set of said ball bearings being located between said first surface section and said first surface portion and said other set being located between said second surface section and said second surface portion.

* * * * *